(12) United States Patent
Rudrabhatla et al.

(10) Patent No.: US 7,547,548 B2
(45) Date of Patent: Jun. 16, 2009

(54) METHOD FOR PRODUCING DIRECT IN VITRO FLOWERING AND VIABLE SEED FROM COTYLEDON, RADICLE, AND LEAF EXPLANTS, AND PLANTS PRODUCED THEREFROM

(75) Inventors: Sairam V. Rudrabhatla, Toledo, OH (US); Stephen L. Goldman, Toledo, OH (US)

(73) Assignee: University of Toledo, Toledo, OH (US)

( * ) Notice: Subject to any disclaimer, the term of this patent is extended or adjusted under 35 U.S.C. 154(b) by 12 days.

(21) Appl. No.: 11/139,929

(22) Filed: May 27, 2005

(65) Prior Publication Data

US 2005/0268357 A1 Dec. 1, 2005

Related U.S. Application Data

(60) Provisional application No. 60/575,645, filed on May 28, 2004.

(51) Int. Cl.
*A01H 4/00* (2006.01)
(52) U.S. Cl. ....................................... 435/426
(58) Field of Classification Search .................. None
See application file for complete search history.

(56) References Cited

OTHER PUBLICATIONS

Franklin et al. 2000, Euphytica, 115:65-73.*
Lin et al. 2003,Plant Cell, Tissue and Organ Culture 72:71-78.*
Singh et al. 2000, Current Science 79:1529-1530.*
Arakawa et al., *Nature Biotechnology* 16:934-938 (1998).
Daniell et al., *Trends in Plant Sciences* 5:219-226 (2001).
Bodhipadma et al., *In vitro Cell Dev. Bio.—Plant* 39:536-539 (2003).
Dielen et al., *J. Exp. Botany*, 52:715-723 (2001).
Franklin et al., *Euphytica*, 115:65-73 (2000).
Galoch et al., *Plant Growth Regulation*, 37: 199-205 (2002).
Lamp et al., *J. Am. Soc. Hort. Sci.* 126: 689-696 (2001).
Lin et al. *Plant Cell, Tissue and Organ Culture*, 72: 71-78 (2003).
Ma et al., *Nature Medicine* 4:601-606 (1998).
Mason et al., *Trends in Biotechnology* 13:388-392 (1995).
Mor et al., *Trends in Microbiology* 449-453 (1998).
Nadgauda et al., *Nature*, 344:335-336 (1990).
Singh et al., *Current Science*, 79:1529-1530 (2000).
Yu et al., *Plant Physiology*, 123:1325-1336 (2000).
Zeitlin et al., *Nature Biotechnology* 16: 1361-1364 (1998).

* cited by examiner

*Primary Examiner*—Elizabeth McElwain
*Assistant Examiner*—Li Zheng
(74) *Attorney, Agent, or Firm*—MacMillan, Sobanski & Todd, LLC

(57) ABSTRACT

The present invention relates to a method of reprogramming plant development that allows flower buds and seeds to arise de novo, directly from a cotyledon or radicle explants or from shoots produced on a cotyledon or radicle. The present invention also provides for an improved culturing media that provide for in vitro flowering.

5 Claims, 7 Drawing Sheets
(7 of 7 Drawing Sheet(s) Filed in Color)

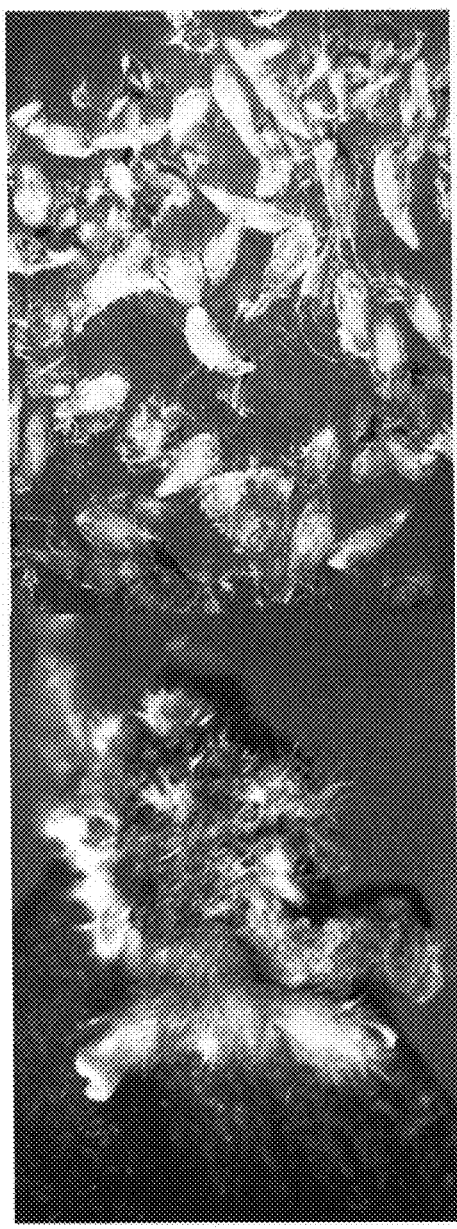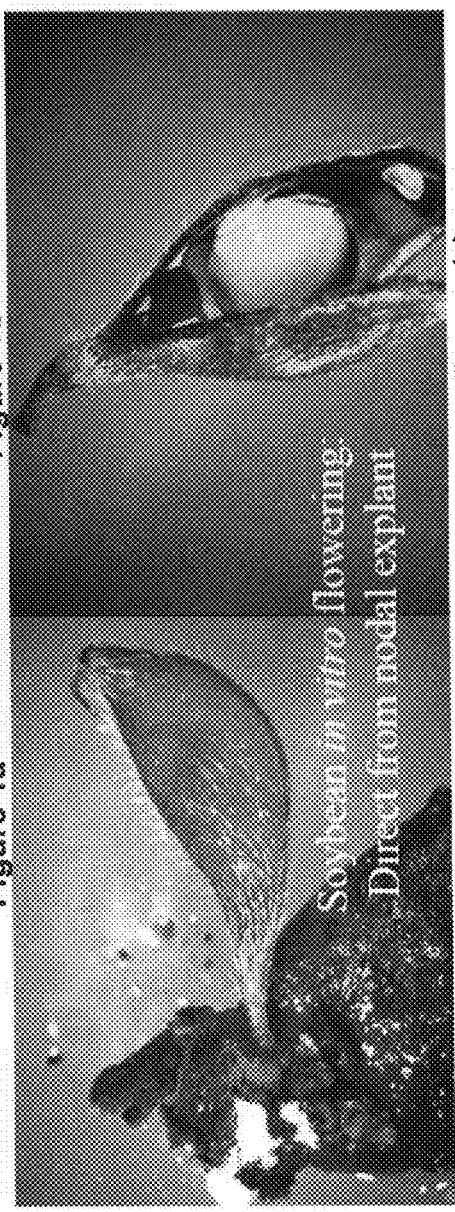

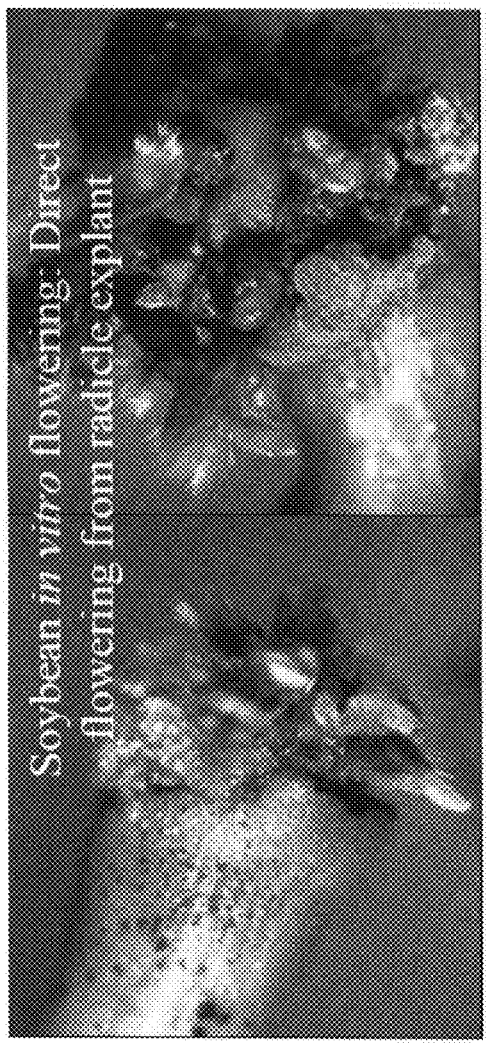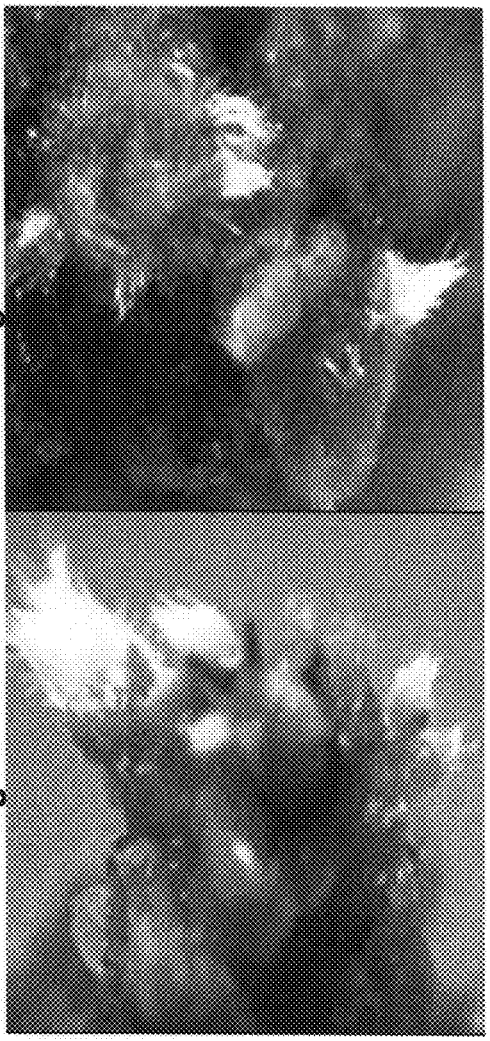

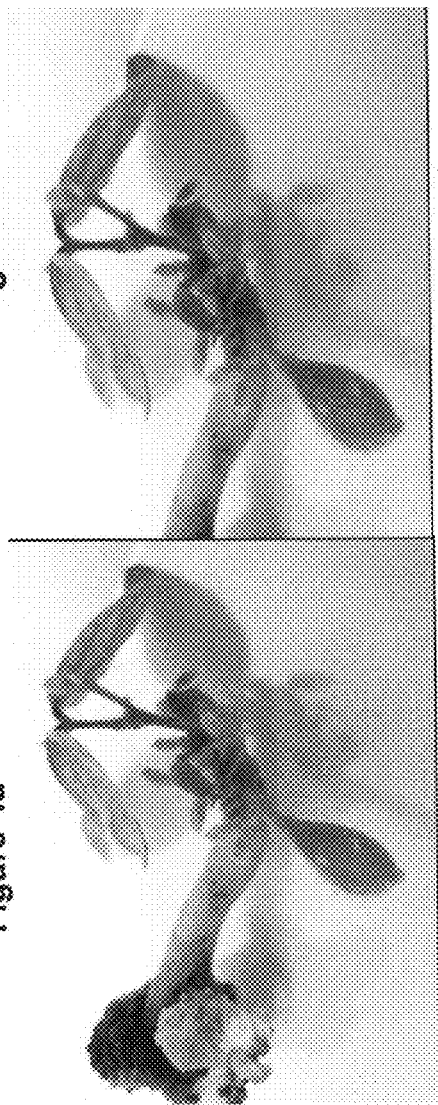
Figure 4a
Figure 4b
Figure 4c
Figure 4d

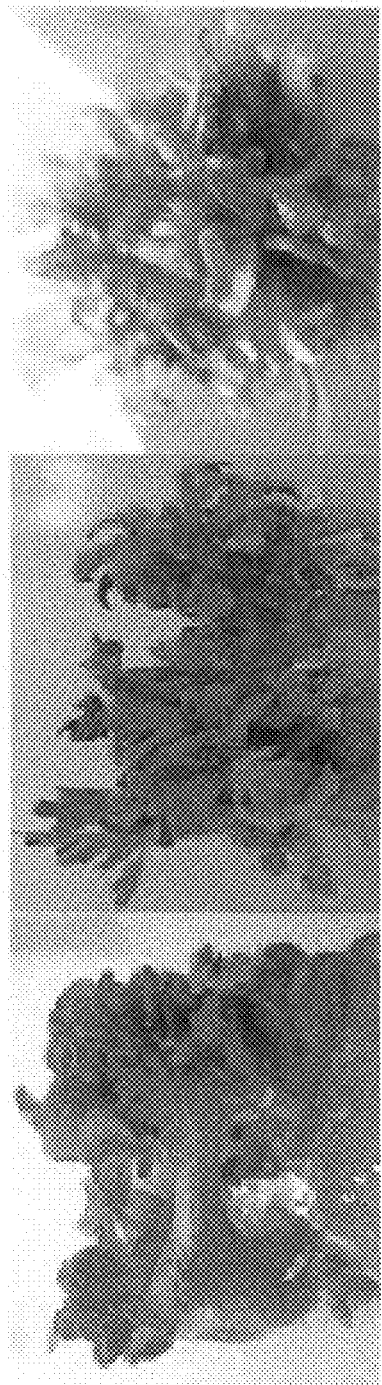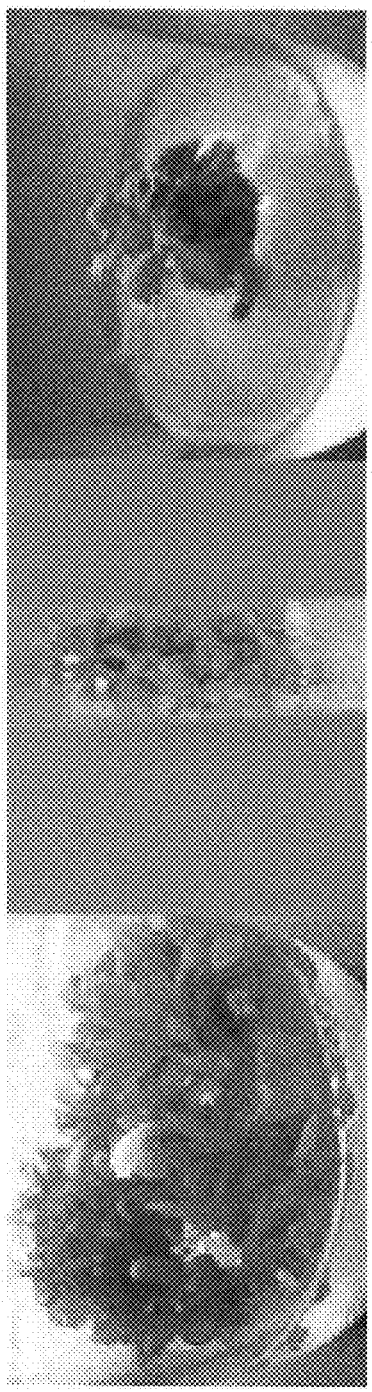
Figure 5a  Figure 5b  Figure 5c  Figure 5d  Figure 5e  Figure 5f

Figure 6a  Figure 6b  Figure 6c  Figure 6d  Figure 6e  Figure 6f

METHOD FOR PRODUCING DIRECT IN VITRO FLOWERING AND VIABLE SEED FROM COTYLEDON, RADICLE, AND LEAF EXPLANTS, AND PLANTS PRODUCED THEREFROM

RELATED APPLICATIONS

This application claims priority to U.S. provisional application 60/575,645, filed on May 28, 2004,which is herein incorporated by reference in its entirety.

This invention was made, at least in part, with government support under USDA-ARS Grant No. 5836071193. The U.S. government has certain rights in the invention.

FIELD OF THE INVENTION

This invention relates to a new method for reprogramming plant development to produce viable seeds from flowers derived directly from cultured cotyledons, radicle explants, and in vitro shoots derived from cotyledons and radicle explants. In particular, by manipulating the cotyledon or radicle or a leaf on a suitable media containing a novel growth regulator regime that affects plant development, it is possible to recover fully fertile, viable-seed producing flowers and either eliminate or reduce significantly the plant body. This "in vitro flowering" provides a significant reduction in the time required for seed production and also eliminates concerns surrounding genetically modified organisms (GMO) relating to pollen contamination, either as is or when supplemented with chloroplast transformation by using our in vitro flowering technique.

BACKGROUND OF THE INVENTION

The national crop germplasm is at risk due to unregulated entry of infected plant materials and to our own mono-culture breeding practices that have lead to the shrinking of our genetic base. The United States Department of Agriculture (USDA) has already identified 2,000 exotic plant pathogens of which 550 have been recognized as posing a threat to US agriculture. One such plant parasite is *Phakospora pachirhzi*, the causative agent of soybean rust. This fungus is native to Asia and has already spread to Africa and to South America, thus posing a significant new threat to the soybean industry both in the United States and abroad. To date, none of our commercially important soybean cultivars have been bred for rust resistance. Indeed, there have been harvest losses due to sensitivity to this fungus in other countries.

Thus, there is a need for a breeding program that would assist in the rapid development of resistant lines against pathogens introduced either by nature, accident or bio-terrorism. The present invention provides a solution to this problem as it provides a robust DNA marker-assisted breeding protocol that allows for rapid development of new lines faster than with traditional breeding programs. Specifically, in vitro flowering allows seed harvest in approximately three months from the time of explant implantation in the tissue culture media, thus enabling, for example, four cycles of soybean production annually.

The methods of the present invention are also especially useful for the incorporation of desirable agronomic traits into plants, including for example, resistance to cold and heat, drought, salt, water stress, insects, pathogens and disease by gene cloning or through DNA marker assisted breeding.

The methods of the present invention are also especially useful for the incorporation of genes that can uptake heavy metals, and accumulate nutrients and trace elements, from contaminated soils, a process referred to as phytoremediation. Phytoremediation employs plants to remediate contaminated soils, typically either by phytostabilization or by phytoextraction. With phytostabilization, plants are used to stabilize contaminated soils by decreasing wind and water erosion as well as decreasing water infiltration and contaminant leaching into groundwater. Phytoextraction attempts to remove contaminants are from the rhizosphere through plant uptake and the contaminants are accumulated in roots, leaves and/or stems. The plant materials are then harvested and the contaminants reclaimed from the plant biomass or the materials are disposed of at a hazardous waste facility.

The methods of the present invention are also especially useful for the production of human interest proteins ("HIP"s) in plants as compared to animal systems. HIPs cover a broad range of commercially important, value-added products that include vaccines, antibodies, hormones, peptides, cytokinins, and enzymes. HIP-based technologies are broad based in their economic impact on greenhouse and farm economy, land value as well as the pharmaceutical industry. By using plants as efficient bio-reactors and synthesizing pharmaceutical product on an acre scale, costs can be reduced for drugs, supplements and food additives.

The completion of the sequencing of the human genome has driven pharmaceutical companies around the world to significantly increase their spending on research and development. In 2001,the pharmaceutical industry spent 30 billion dollars alone on drug design. This figure represents a 19% increase over that spent in 2000.

As reported by the Pharmaceutical Research and Manufacturers of America, more than 1,000 drugs are in clinical studies or are awaiting final approval from the Food and Drug Administration. Of these, 400 address cancer therapies, 200 for special needs children, 100 each for heart disease and stroke, 26 for Alzheimer's disease, 25 for diabetes, 19 for arthritis, 16 for Parkinson's disease and 14 for osteoporosis. Collectively the industry must be prepared to accept the inevitable pressure of designing manufacturing systems that will control drug costs. Today state-of-the-art production of genetically engineered proteins is through mammalian cell culture. A minimum investment of $100 million is needed to build a factory that will produce a mere couple of hundred grams of product annually. As this does not usually generate sufficient quantities, third world countries will face ensuing hardships as they often cannot afford the startup costs and/or lack a sufficient number of trained personnel to produce their own medications.

Moreover, the use of mammalian cell culture as bio-reactors for HIP production carries with it certain intrinsic health risks. Specifically, an inherent danger of viral contamination associated with mammalian-derived materials necessitates exhaustive safety testing and validation of production processes. Animals infected with certain zoonotic viruses have transmitted fatal illnesses to humans. Numerous mouse-derived cell lines contain endogenous retroviruses and some demonstrate species-specific tumorigenic potential. Oncogenic xenotropic murine retroviruses are of particular concern because of the many theoretical risks they present to humans. New viruses with altered pathogenicity or host range could be generated through genetic recombination. Tumors also may form through integration of the viral genome in close proximity to a host oncogene, thus activating the oncogene.

Thus, given the issues above, the plant biotechnology sector has a great interest in expressing mammalian proteins in plants in a way that would allow their commercial exploitation. The advantages of producing therapeutic recombinant proteins in plants are many. These include the ability to fabricate HIP production on an agricultural scale, which significantly lowers manufacturing costs. Further, one may possibly transport highly sought and needed therapeutic proteins that remain stable in dry seed for extended periods of time. Most importantly, no human or animal pathogens have ever been reported that have the ability to infect plants. Thus, viral contamination that is observed in animal cell culture is absent in plants.

Already, transgenic plants have been produced to express a number of different HIP molecules using a variety of plant species. See e.g. Mason and Amtzen, *Trends in Biotechnology* 13:388-392 (1995); Arakawa et al., *Nature Biotechnology* 16:282-297 (1998); Mor et al., *Trends in Microbiology* 449-453 (1998); Ma et al., *Nature Medicine* 4:601-605 (1998); Zeitland et al., *Nature Biotechnology* 16: 1361-1364 (1998). Transgenic potato plants are producing HIP that are responsive to diabetes, and to cholera (a disease that affects five million people annually and kills 200,000) and to enterotoxigenic *Escherichia coli* (ETEC), the leading cause of diarrhea in children under five in third world nations. ETEC pathology is profound and results in 650 million cases of diarrhea that kills 800,000 children annually (Block, 1986).

In tobacco, a surface protein from *Streptococcus mutans* is being synthesized that should confer passive immunity with respect to tooth decay. Additionally, tobacco is being used to produce a second vaccine against Hepatitis B, an infectious disease that annually cripples two billion people. Unfortunately, the levels of gene expression that have been observed in tobacco are low and often disturbingly variable. See also Daniell et al., *Trends in Plant Sciences* 5:219-226 (2001).

Despite the advance in the production of HIP in plants, issues remain to be resolved. For example, differences in HIP production have not only been delineated among plants of different cultivars but also among plants from the same cultivars. Low output and variable gene expression is not the only problem that is encountered in these production systems. Some plants are easy to engineer, but produce HIP that cannot be ingested or easily purified. For example, the leaves of tobacco contain toxic alkaloids and therefore cannot be eaten. Alternatively, attempts to purify proteins from transgenic tobacco leaves also are compromised due to the abundant phenolic contamination. Similarly, the utility of transgenic potatoes is limited as the raw tuber is not especially palatable. The amounts needed to ingest a therapeutically active dose would be difficult to tolerate. Moreover, the average potato contains only two percent protein of which the HIP is likely to be a minor component.

In contrast, some transgenic plants like tomato and banana are easily ingested, however, their utility as sources of edible HIP is compromised by the fact that the amount of protein found in these fruits is low, which no doubt limits the amount of HIP made. Furthermore, banana transformation rates are low and each transgenic fruiting banana plant requires a minimum of two years from the time of genetic manipulation to harvest.

Grains, such as corn, are more suitable bioreactors than bananas. Specifically, palatable seed can be easily produced in large numbers using relatively unsophisticated farming techniques. Unfortunately, corn has several major limitations. The amount of protein/seed is low and growing sufficient amounts in contained quarters would be difficult. Further, transgenic corn pollen travels on average 600 feet, and would pose containment problems that are significantly reduced using other plants.

Thus, there remains a need for a robust alternative HIP bio-reactor technology where speed of delivery is linked to high quantity protein production and problems associated with pollen containment are drastically reduced. The present invention satisfies this need through the production of transgenic plants in a contained environment through a novel in vitro flowering method. The present invention provides speed of delivery linked to high quantity protein production as well as drastically reducing problems and costs associated with pollen containment issues.

Although, in vitro flowering has been previously observed in capsicum, bamboo and in orchids (Yu and Goh, *Plant Physiology*,vol. 123, 1325-1336 (2003); Bodhipadma and Leung, *In Vitro Cellular and Developmental Biology Plant* 39(5) September-October 2003, 536-539 (2003); and Ho and Chang "In Vitro Flowering of Albino Bamboo (Bambusa Oldhamnii Munro) Regenerants Derived from an Eleven-Year Old Embryogenic Cell Line" 2003 ISHS Acta Horticulturae 461: International Symposium on Biotechnology of Tropical and Subtropical Species Part 2 (2003)), there remains a need for in vitro flowering methods that produce viable seeds from the flowers. In these previous in vitro flowering experiments, the in vitro flowers were induced in tissue culture from intervening stem or modified stem-like structure, but failed to produce viable seed.

SUMMARY OF THE INVENTION

The present invention provides a method for eliciting direct flower bud production in vitro on a cotyledon. This method involves germinating a seed on a $MSB_5$ medium and splitting the two cotyledons. A cotyledon is transferred to a cotyledon-flowering medium. The cotyledon-flowering medium (which is also an embodiment of the present invention) comprises $MSB_5$ medium augmented with at least one substituted phenylurea cytokinin analog (preferably TDZ at a concentration of about 1.5 mg/L to 2.5 mg/L). The cotyledon-flowering medium may further comprise a cytokinin (preferably BAP at a concentration of about 0.75 mg/L to 1.5 mg/L). After flower bud initiation occurs on the cotyledon, the cotyledon is transferred to $MSB_5$ medium and is allowed develop flowers and may further be allowed to develop seed.

In another embodiment, the above method is combined with transformation of the cotyledon (using methods known in the art) with a gene of interest to develop viable transgenic seeds.

Another embodiment of the invention provides a method for eliciting flower bud production on in vitro developed shoots from a cotyledon. This method involves germinating a seed on a $MSB_5$ medium and splitting the two cotyledons. A cotyledon is transferred to a cotyledon-shoot flowering medium (which is also an embodiment of the present invention). The cotyledon-shoot flowering medium comprises a $MSB_5$ medium augmented with at least one substituted phenylurea cytokinin analog (preferably TDZ at a concentration of 0.75 mg/L to 2.5 mg/L) and a cytokinin (preferably BAP at a concentration of 2.5 mg/L to 3.5 mg/L). After shoot initiation occurs on the cotyledon, it is transferred to $MSB_5$ medium and is allowed to develop flowers and may further be allowed to develop seed.

In another embodiment, the above method is combined with transformation of the cotyledon (using methods known in the art) with a gene of interest to develop viable transgenic seeds.

In another embodiment of the invention, there is provided a method for eliciting direct flower bud production in vitro on a radicle. This method involves germinating a seed on a $MSB_5$ medium and removing the radicle from the seed. The radicle is transferred to a radicle-flowering medium (which is also an embodiment of the present invention). The radicle-flowering medium comprises a substituted phenylurea cytokinin analog (preferably TDZ at a concentration of 1.5 mg/L to 2.5 mg/L). The radicle-flowering medium may further comprise a cytokinin (preferably BAP at a concentration of 0.75 mg/L to 1.5 mg/L).

After flower bud initiation occurs on the radicle, the radicle is transferred to $MSB_5$ medium and is allowed develop flowers and may further be allowed to develop seed.

In another embodiment, the above method is combined with transformation of the radicle (using methods known in the art) with a gene of interest to develop viable transgenic seeds.

Another embodiment of the invention provides a method for eliciting flower bud production on in vitro developed shoots from a radicle. This method involves germinating a seed on a $MSB_5$ medium and then removing the radicle. The radicle is transferred to a radicle-shoot-flowering medium (which is also an embodiment of the present invention). The radicle-shoot-flowering medium comprise sa $MSB_5$ medium augmented with at least one substituted phenylurea cytokinin analog (preferably TDZ at a concentration of 0.75 mg/L to 2.5 mg/L) and a cytokinin (preferably BAP at a concentration of 2.5 mg/L to 3.5 mg/L). After shoot initiation occurs on the radicle, it is transferred to $MSB_5$ medium and is allowed to develop flowers and may further be allowed to develop seed.

In another embodiment, the above method is combined with transformation of the radicle (using methods known in the art) with a gene of interest to develop viable transgenic seeds.

Another embodiment of the present invention provides a method for eliciting flower bud production on in vitro developed shoot from a leaf explant. This method involves germinating a leaf explant on an in vitro shoot multiplication medium comprising MS medium supplemented with an auxin (preferably IAA at a concentration of 0.05 mg/L to 0.25 mg/L) and a cytokinin (preferably BAP at a concentration of 1.75 mg/L to 2.25 mg/L). Preferably GA 3 is present at a concentration of 0.1 mg/L to 1 mg/L. The leaf explant is allowed to develop a shoot, which is then transferred to an in vitro shoot elongation medium. The in vitro shoot elongation medium comprises a gibberellic acid. The shoot is allowed to elongate and then transferred to a MS medium where it is allowed to develop at least one flower bud, and may further be allowed to develop seed.

In another embodiment, the above method is combined with transformation of the leaf explant (using methods known in the art) with a gene of interest to develop viable transgenic seeds.

BRIEF DESCRIPTION OF THE DRAWINGS

The patent or application file contains one or more drawings executed in color and/or one or more photographs. Copies of this patent or patent application publication with color drawing(s) and/or photograph(s) will be provided by the Patent Office upon request and payment of the necessary fee.

FIGS. 1a-1d are photographs showing direct viable-seed producing flower bud production from cotyledons in soybean.

FIGS. 3a-3d are photographs showing direct viable-seed producing flower buds from radicle explants in soybean.

FIGS. 4a-4d are photographs showing viable-seed producing flower bud production from in vitro developed shoots from radicle explants in soybean.

FIGS. 5a-5f are photographs showing in vitro flowering in chrysanthemum palludosum.

FIGS. 6a-6f are photographs showing in vitro regeneration and flowering of Centaurea monatana and Centaurea cyanus.

DETAILED DESCRIPTION OF THE INVENTION

Definitions

Figures 2A, 2B:
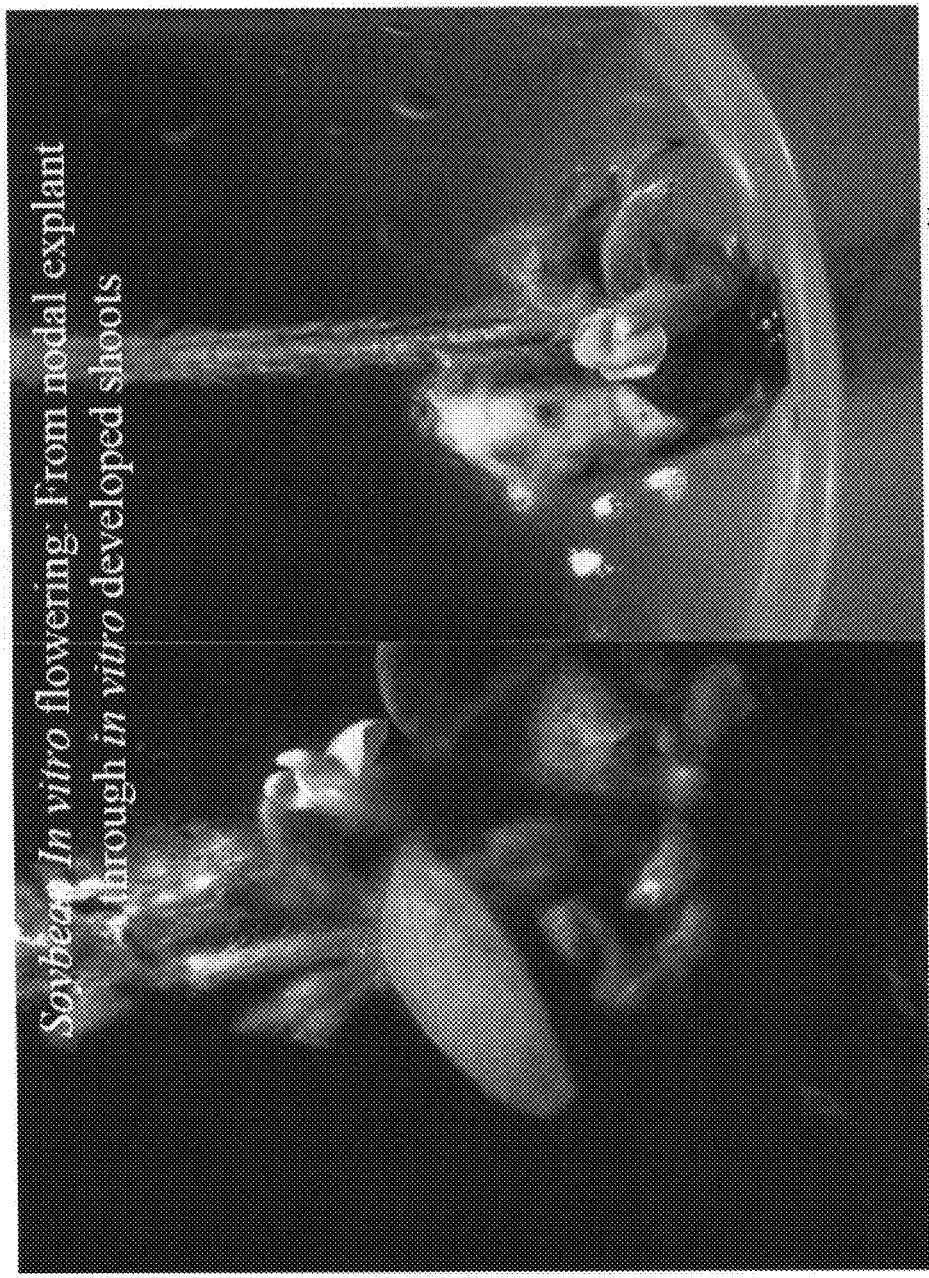
FIGS. 2a and 2b are photographs showing direct viable-seed producing flower buds from in vitro shoots in soybean.

In order to provide a clear and consistent understanding of the specification and claims, including the scope to be given to such terms, the following definitions are provided.

We define "in vitro flowering" as direct fertile flower production and viable seed production from an explant without a plant body. Given cells of an explant are reprogrammed to terminate vegetative meristem and lead directly to a reproductive state leading to flower and seed production. The immediate result of in vitro flowering is the production of fertile flowers that gives raise to viable seed. In vitro flowering encompasses precocious flowering where the flowers are produced directly from explants having a reduced life cycle but nevertheless produce viable seed. The in vitro flowering of the present invention provides methods of eliciting different developmental fates from cells of an explant by application of a unique novel growth regulator regime. These developmental fates include, but are not limited to: (1) direct viable-seed producing flower bud production on cotyledons leading to the formation and recovery of fertile seed; (2) direct viable-seed producing flower bud production from individual in vitro developed shoots from cotyledon explants leading to the formation of fertile flowers and recovery of viable seed; (3) direct viable-seed producing flower bud production from radicle explants leading to the formation of fertile flowers and recovery of viable seed; and (4) direct viable-seed producing flower bud production from in vitro developed shoots from radicle explants leading to the formation of fertile flowers and recovery of viable seed. Additional developmental fates include production of flower buds and viable seed from in vitro developed shoots from leaf explants. These directed cell fate shifts result from a manipulation of growth regulators in defined concentrations and/or combinations that dictate the cell fate shifts of each explanted tissue.

These directed developmental fates have been identified in response to different growth regulators, in combination or alone, and as a function of growth regulator concentration, time of application, and choice of explanted tissue. The present invention also provides novel in vitro flowering media, which constitute a unique advance in the field of cell fate determination since different hormonal combinations in combination with a specified explant control different developmental outcomes (e.g. the same meristematic cells will respond differentially to different hormonal combinations). For example, cotyledon explants will produce only shoots with one set of hormone combination (3.0 mg/1 BAP) and only flowers and viable seeds with another hormone profile (2.0 mg/1 TDZ and 1.0 mg/1 BAP).

"Untransformed cells" as used herein refers to cells that have not been contacted with a particular DNA fragment or gene of interest, which will be used when applying the method of the invention. Such cells may also be derived from a transgenic plant or plant tissue that had been previously transformed with a different or similar DNA fragment or gene of interest.

"Efficiency of transformation" or "frequency of transformation" as used herein refers to the likelihood that a population of cells/plants will be transformed with a gene of choice. "Efficiency of transformation" or "frequency of transformation" can be measured by the number of transformed cells/plants (or transgenic organisms grown from individual transformed cells) that are recovered from a population of cells.

A "transgenic plant" as used herein contains cells that replicate a gene of interest (referred to herein as a "delivered gene") and pass the gene of interest to each daughter cell in each generation and to the progeny of the next. The gene of interest may be covalently linked either to nuclear DNA and/or plastid DNA. As a result, the delivered gene is integrated in the DNA and passes from one generation to the next. Plastid DNA is maternally inherited during sexual reproduction. The delivered gene(s) include DNA from a wide range of plant, animal, fungal, bacterial, viral, and protists sources, as well as DNA homologous to the recipient plant. The delivered gene can include selectable and/or screenable markers. However, a delivered gene need not be linked to a selectable marker. In this case, transgenic cells can be identified following co-transformation using two separate agrobacterium plasmids. Transgenic plants express at least one additional homologous, foreign or plant-optimized gene. Transgenic plants may be produced using the method of the present invention by combining in vitro flowering with a transformation method, and, and subsequent regeneration of the plant from the transformed cells. Acceptable transformation methods are known in the art and include, but are not limited to, agrobacterium-mediated-transformation, chloroplast transformation, biolistics, electroporation, polyethylene glycol ("PEG") mediated transformation, protoplast mediated DNA uptake, and whisker mediated transformation.

"MS basal medium" is known in the art and was originally described by Murashige and Skoog, *Physiology Plantarum* 15:473-497 (1962). In the methods and media of the present invention, "MS basal medium" or "MS medium" as used herein includes MS basal medium as described by Murashige and Skoog as well as equivalents of MS basal medium. One skilled in the art would understand that equivalents of MS basal medium include media that is substantially similar in contents and concentrations of salts, chemicals, etc., such that a tissue or plant would develop/grow in the same manner when exposed to MS basal medium.

MS basal medium with $B_5$ vitamins ("$MSB_5$ medium") is known as was originally described by Gamborg, O. L.; Miller, R. A.; Ojima, K., *Exp. Cell Res.* 50:151-158 (1968). In the methods and media of the present invention, "$MSB_5$" as used herein includes MS basal medium as described by Murashige and skoog and $B_5$ vitamins as described by Gamborg as well as equivalents of $MSB_5$. One skilled in the art would understand that equivalents of $MSB_5$ include media that is substantially similar in contents and concentrations of salts, chemicals, vitamins, etc. such that a tissue or plant would develop/grow in the same manner when exposed to $MSB_5$.

"Plant growth regulators" as used herein, is a synonymous term with "Plant Hormones." "Plant growth regulators" or "plant hormones" as used herein are those hormones that promote root induction, cell division and cell elongation that lead to the formation of shoots, roots, flowers and seed. Plant growth regulators have been commonly classified into five groups: auxins, cytokinins, gibberellins, ethylene and abscisic acid.

"Auxins" include, but are not limited to, naturally occurring and synthetic auxins. Naturally occurring auxin is indole acetic acid ("IAA"), which is synthesized from tryptophan. An exemplary synthetic auxin in dichlorophenoxyacetic acid ("2,4-D"). Other auxins include, but are not limited to, 4-chlorophenoxyacetic acid ("4-CPA"), 4-(2,4-dichlorophenoxy)butyric acid ("2,4-DB"), tris[2-(2,4-dichlorophenoxy)ethyl] phosphite ("2,4-DEP"), 2-(2,4-Dichlorophenoxy) propionic acid ("dicloroprop"), (RS)-2-(2,4,5-trichlorophenoxy)propionic acid ("fenoprop"), naphthaleneacetamide, α-naphthaleneacetic acid ("NAA"), 1-naphthol, naphthoxyacetic acid, potassium naphethenate, (2,4,5-trichlorophenoxy)acetic acid ("2,4,5-T"), indole-3-acetic acid, indole-3-butyric acid ("IBA"), 4-amino-3,5,6-trichloropyridine-2-carboxylic acid ("picloram"), 3,6-dichloro-o-anisic acid ("dicamba"), indole-3-proionic acid ("IPA"), phenyl acetic acid ("PAA"), benzofuran-3-acetic acid ("BFA"), and phenyl butric acid ("PBA"). A primary site of auxin production is the apical shoot meristem and the most studied function of auxin is the promotion of elongation and cell enlargement. Auxins also promote lateral and adventitious root development.

"Cytokinins" are a group of phenylurea derivatives of adenine. Cytokinins promote cytokinesis (division of the cytoplasm to a cell following the division of the nucleus). Cytokinins also retard leaf senescence. The first naturally occurring cytokinin chemically identified was called zeatin. An exemplary synthetic cytokinin is 6-benzylamino purine ("BAP"). Examples of cytokinins include, but are not limited to, 6-γ,γ-Dimethylallylaminopuine ("2iP"), kinetin, zeatin, zeatin riboside, and BAP.

"Substituted phenylurea cytokinin analogs" are cytokinin analogs and have cytokinin-like activity. It is believed that these analogs are not metabolized by plants. "Substituted phenylurea cytokinin analogs" as used herein include, but are not limited to, 1-phenyl-3-(1,2,3-thiadiazol-5-yl)urea ("thidiazuron" or "TDZ"), carbanilide (1,3,-diphenyl urea) ("DPU"), and N-(2-chloro-4-pyridyl)-N'-phenylurea ("CPPU").

Giberrellins are derived from the ent-gibberellane skeleton. Gibberellins are diterpenes synthesized from acetyl CoA via the mevalonic acid pathway. They all have either 19 or 20 carbon units grouped into either four or five ring systems. The gibberellins are named $GA_1 \ldots GA_n$ in order of discovery. Gibberellic acid, which was the first gibberellin to be structurally characterized, is GA3,and is the most commonly used gibberreilin. There are currently 136 GAs identified from plants, fungi and bacteria. Giberrellins are generally used to promote flowering, break dormancy of seeds, buds, corms, and bulbs, and cause stem elongation.

"Gene" as used herein includes any informational hereditary unit including regulatory sequences as well as those nucleic acid sequences involved in protein expression within the cells (including both prokaryotic and eukaryotic), including chimeric DNA constructions, plant genes and plant-optimized genes.

"Plant gene" as used herein means a gene encoded by a plant.

"Plant-optimized gene" as use herein means a homologous or heterologous gene designed for plant expression.

"Gene of interest" or "delivered gene" may be homologous DNA, heterologous DNA, foreign DNA, genomic DNA or cDNA.

"Stacked genes" of interest are those containing more than one gene(s) that confers value-added traits or phenotypes linked to between either the right and left T-DNA border sequences or covalently linked to the right border sequence. Alternatively, stacked genes refers to a multiple of genes that have been delivered and integrated in the host DNA of the plant cell by more than one recombination event, as in the case of co-transformation. In co-transformation, the T-DNA constructs are in independent *Agrobacterium* strains.

"Expression" means the transcription and stable accumulation of the mRNA and/or protein within a cell. Expression of genes involves transcription of DNA into RNA, processing of the RNA into mRNAs in eukaryotic systems, translation of mRNA into precursor and mature proteins, followed, in some cases, by post-translational modification. This definition in no way limits expression to a particular system and is meant to include all types including cellular, transient, in vitro, in vivo, and viral expression systems in both prokaryotic and eukaryotic cells.

"Organogenesis" means a process by which shoot and roots are developed sequentially under in vitro conditions from any meristematic tissue.

"Embryogenesis" is a process of differentiation that is characterized by the formation of organized structures that resemble zygotic embryos from which shoots and roots may be produced in vitro.

"Whisker-mediated transformation" is the facilitation of DNA insertion into plant cell aggregates and/or plant tissues by elongated needle-like microfibers or "whiskers" and expression of said DNA in either a transient or stable manner. (See e.g. U.S. Pat. Nos. 5,302,523 and 5,464,765,which are herein incorporated by reference).

The present invention provides a method to produce flowers and viable seeds in vitro that are especially useful for multiplication of seed with value-added traits generated through conventional breeding and/or for rapid and efficient production of transgenic seeds under conditions of complete pollen containment. In this connection, either transgenic or non-transgenic seed can be recovered following in vitro flowering in a reduced amount of time as compared to natural seed production. For example, using the methods of the present invention, soybean seed is routinely produced in three months. This reduces the harvest time by about 50% as compared to a harvest time previously reported by Goldman and Sairam, U.S. patent application Ser. No. 10/480,865 filed on Dec. 12, 2003,and WO 02/102979 entitled "Methods for Transformation of Mono- and Dicotyledonous Plants Using Meristematic Tissue," which references are herein incorporated by reference in their entireties.

In addition, using the methods of the present invention, seed can be recovered from flower buds developed directly on cotyledons, radicle explants or from in vitro developed shoots from radicle or cotyledon explants. The technology of the present invention is also especially useful for year-round farming of cultivated and wild species of economically important plants. The technology of the present invention is also characterized by its robustness with respect to seed recovery. For example, the average soybean plant under farm conditions produces approximately 100 seeds. By contrast, using the methods of the present invention relating to in vitro flowering, it is possible to recover up to 80 seeds per petri dish containing at least four cotyledons by any of the above mentioned developmental fates. Since the methods of the present invention provide seed production in a controlled environment (e.g. tissue culture or greenhouse), risks of pathogen infection, costs associated with the use of fertilizers, herbicides, and insect sprays, and fears of pollen contamination are ameliorated.

Many medicinal and floral plants are considered as endemic or threatened due to the environmental stress and pressure they live under. Proper management and protection is required for the conservation of these plant species, such as *Centaurea montana* and *Centaurea cyanus*. In vitro regeneration and micropropagation as provided by the in vitro flowering methods of the present invention provide powerful tools for the conservation of these plant species.

Direct Fertile Flower Bud and Viable-Seed Production on Cotylendon

The present invention provides various methods to direct cells of a certain explants to a desired cell fate. Accordingly, one embodiment of the present invention provides a method for producing viable seed from a flower bud directly produced on a cotyledon. This method comprises germinating a seed having intact cotyledons on MS basal medium with $B_5$ vitamins ("MSB$_5$ medium"). See Gamborg, O. L.; Miller, R. A.; Ojima, K., *Exp. Cell Res.* 50:151-158; 1968. Any seed, monocot or dicot, may be used, including but not limited to those in the family asteraceae, solanaceae or fabaceae. In addition to using a seed that may or may not be transformed with a gene of interest using the methods of the present invention described herein below, a seed generated from a transgenic plant (thus already having a gene of interest) may also be used.

Preferably before germination, the seeds are washed in running tap water with a drop of soap for 15 mins and sterilized with 70% ethyl alcohol for 1 min followed by a 10 minute treatment with 0.1% mercuric chloride and washed three times for 5 min intervals with sterile distilled water. Six seeds are germinated in each petriplate with MSB5 medium After germination on a MSB$_5$ for a period of time, such as 3 days in the dark at 24±2° C., both the cotyledons are split and the radicle and embryo are removed. The isolated cotyledons from the seed are plated on cotyledon-flowering medium (which is another embodiment of the invention and is described in detail below). The cotyledon-flowering medium preferably comprises a substituted phenylurea cytokinin analog, such as TDZ and a cytokinin such as BAP.

If desired, the cotyledon may be transformed at this time with any suitable technique known in the art. Preferably the abaxial side of a cotyledon is placed in contact with a cotyledon-flowering medium. Cultures are incubated at 24±2° C. under a 16/8-hour dark photoperiod provided by cool-white fluorescent lights at a quantum flux density of 30 $\mu$mol s$^{-1}$m$^{-2}$.

Following a passage of time, typically within 3 weeks, flower bud initiation occurs on a cotyledon having been placed on a cotyledon-flowering medium. After about 3 weeks, cotyledons are transferred to MSB$_5$ medium. The flower bud continues to grow on MSB$_5$ medium to develop and produce viable seeds. During this time, cultures are incubated with necessary light-dark photoperiodic conditions to promote growth and to mimic natural growing conditions. Additionally, over time it may be necessary to subculture the explants with fresh MSB$_5$ medium. See example 1 and FIGS, 1a-1d for direct viable-seed producing flower bud initiation on a soybean cotyledon.

This method as well as the other methods of the present invention described herein below may also be practiced in other tissue culture systems in addition to petri dishes. One skilled in the art would appreciate that other acceptable plant tissue culture systems exist. For example, the use of Magenta™ vessels, Magenta™ Membrane Raft, or Osmotek's Life Raft may be successfully employed.

Cotyledon-Flowering Medium

Another embodiment of the invention provides a cotyledon-flowering medium comprising MSB$_5$ medium and at least one substituted phenylurea cytokinin analog. A cotyledon placed on a cotyledon-flowering medium produces flower buds that produce fertile seed. An exemplary substituted phenylurea cytokinin analog is (N-phenyl-N'-1,2,3-thidiazol-5-ylurea)(also known as "Thidiazuron" or "TDZ").

TDZ is a bio-regulator of morphogenesis in tissue culture of many plant species. A substituted phenylurea cytokinin analog or mixtures thereof may be present in the cotyledon-flowering medium at a concentration of about 0.1 mg/L to about 5.0 mg/L (and any concentration within that range), alone or in combination with a cytokinin and/or auxin as described below. A preferred concentration of a substituted phenylurea cytokinin analog is about 1.0 mg/L to about 4.0 mg/L. A more preferred concentration is about 1.5 mg/L to about 3.0 mg/L. An especially preferred concentration of a substituted phenylurea cytokinin analog is about 1.5 mg/L to about 2.5 mg/L. A most preferred concentration of a substituted phenylurea cytokinin analog is about 2.0 mg/L.

In preferred embodiments, a substituted phenylurea cytokinin analog is TDZ and is present in a cotyledon-flowering medium at a concentration of about 0.1 mg/L to about 5.0 mg/L (and any concentration within that range), alone or in combination with other cytokinins and/or auxins as described below. A preferred concentration of TDZ is about 1.0 mg/L to about 4.0 mg/L. A more preferred concentration of TDZ is about 1.5 mg/L to about 3.0 mg/L. An especially preferred concentration of TDZ is about 1.5 mg/L to about 2.5 mg/L. A most preferred concentration of TDZ is about 2.0 mg/L.

A cotyledon-flowering medium may also contain plant hormones, known as cytokinins. Exemplary cytokinins include but are not limited to benzyl amino purine ("BAP"), zeatin, and kinetin, as well as others discussed above in the definitions and as known by one skilled in the art. Cytokinins play an important physiological effect on plant growth and morphology as they promote shoot formation and lateral bud expansion and delay leaf senescence through their functions in promoting cell division and cell differentiation.

Cytokinin(s) or mixtures thereof may be present in a cotyledon-flowering medium at a concentration of about 0.5 mg/L to about 4.0 mg/L (and any concentration within that range). A preferred concentration is about 0.5 mg/L to about 3.0 mg/L. A more preferred concentration is about 0.75 mg/L to about 2.5 mg/L. An especially preferred concentration of cytokinin is about 0.75 mg/L to about 1.5 mg/L. A most preferred concentration of BAP is about 1 mg/L.

In preferred embodiments, a cytokinin is BAP and may be present in a cotyledon-flowering medium at a concentration from about 0.5 mg/L to about 4.0 mg/L (and any concentration within that range). A preferred concentration of BAP is about 0.5 mg/L to about 3.0 mg/L. A more preferred concentration of BAP is about 0.75 mg/L to about 2.5 mg/L. An especially preferred concentration of BAP is about 0.75 mg/L to about 1.5 mg/L.

When TDZ (2.0 mg/L) is combined with BAP (1.0 mg/L), cell fate is altered and flowers are produced directly on a cotyledonary explant. While this hormone combination is preferred, other combinations and concentrations of cytokinins also produce flowers directly on a cotyledon. For example, TDZ (1.0-2.0 mg/L) without BAP also produces flowers on cotyledonary explants. It appears that TDZ concentration in an in vitro flowering medium is an important parameter in reducing or increasing flower bud formation. For example concentrations of TDZ below 1.0 mg/L induced fewer number of flowers and less frequently. Even though frequent flower induction was noticed on medium containing only 1.0 to 2.0 mg/L TDZ, they were short, vitrified and abnormal. At a concentration of 5.0 mg/L TDZ, neither flower induction nor shoot induction was noticed. Thus, a preferred cotyledon flowering medium comprises about 2.0 mg/L TDZ and about 1.0 mg/L BAP.

A cotyledon-flowering medium of the present invention may also contain auxins in addition to, or instead of, cytokinins. Exemplary auxins include, but are not limited to, naphthalene acetic acid ("NAA"), indole acetic acid ("IAA"), 2,4-dicholoropehonoxyacetic acid ("2,4-D"), indole-3-proionic acid ("IPA"), indole-3-butyric acid ("IBA"), phenyl acetic acid ("PAA"), benzofuran-3-acetic acid ("BFA"), phenyl butric acid ("PBA"), dicamba, picloran and others discussed above in the definitions and known by one skilled in the art. Auxins also play an important role on plant growth and morphology in that they promote apical dominance, lateral and adventitious root formation, stem elongation and leaf elongation by promoting cell elongation. A preferred auxin is NAA and maybe present in a cotyledon-flowering medium at a concentration of about 0.1 mg/L to about 0.4 mg/L. A preferred concentration of NAA is about 0.2 mg/L. In one embodiment of the invention, a cotyledon-flowering medium comprises about 2.0 mg/L TDZ alone, or in combination with, about 0.2 mg/L NAA.

A cotyledon-flowering medium is prepared by supplementing a $MSB_5$ medium with a desired substituted phenylurea cytokinin analog, and/or a cytokinin, and/or auxin, or mixtures thereof as described above. The medium is augmented with 3% sucrose. If the medium is to be used on a solid state culture, e.g. petri dish, the medium is solidified with 0.5 to 0.75% agar (Phytochech Labs). The pH of the medium is adjusted to 5.8 with 0.1 M NaOH or 0.1 M HCl before autoclaving at 1.4 kg cm$^{-2}$ for 20 mins at 121° C. After sterilization 20 ml of this medium is dispensed in to each sterile petriplate (100×15 mm).

Fertile Flower Bud and Viable-Seed Production from in Vitro Developed Shoots from Cotyledon One embodiment of the present invention provides the ability to induce multiple shoots leading to fertile flowers and viable seeds under in vitro conditions. This directed cell development fate relates to a method for eliciting flower bud production from individual in vitro developed shoots from cotyledon explants leading to the formation and recovery of fertile seed. The preparation of seeds, cotyledons, explants, media and sterilization procedures are known in the art and are as described above.

In this method, the isolated cotyledons from the germinated seed are plated on a cotyledon-shoot-flowering medium (which is another embodiment of the invention and is described below). A cotyledon-shoot flowering medium preferably comprises a cytokinin or mixtures thereof, such as BAP or combinations of cytokinins and a substituted phenylurea cytokinin analog such as TDZ or mixtures thereof. If desired, the cotyledon may be transformed at this time with any suitable technique known in the art. Preferably the abaxial side of the cotyledon is placed in contact with a cotyledon-shoot-flowering medium. Cultures are incubated at 24×2° C. under a 16/8-hour dark photoperiod provided by cool-white fluorescent lights at a quantum flux density of 30 $\mu mol\ s^{-1} m^{-2}$.

Following a passage of time, typically, within four to six weeks, shoot initiation occurs on a cotyledon having been placed on a cotyledon-shoot-flowering medium. The shoot continues to grow and develop a flower bud within two to four weeks after shoot initiation. The explant is maintained on a cotyledon-shoot flowering medium for about 15 days and then transferred to $MSB_5$ medium.

During this time, cultures are incubated with necessary light-dark photoperiodic conditions to promote growth and to mimic natural growing conditions. Additionally, over time it may be necessary to subculture the explants with fresh $MSB_5$ medium. See example 2 and FIGS. 2a-2b for fertile flower bud and viable-seed production from in vitro developed shoots from cotyledon.

Cotyledon-Shoot-Flowering Medium

Another embodiment of the invention provides a cotyledon-shoot-flowering medium comprising $MSB_5$ medium and a substituted phenylurea cytokinin analog (as described above), or mixtures thereof. A cotyledon placed on a cotyledon-shoot-flowering medium produces shoots in vitro, which produces flower buds that produce fertile seed. A cotyledon-shoot-flowering medium of the present invention may further comprise a cytokinin (as described above) or mixtures thereof. A substituted phenylurea cytokinin analog may be present in a cotyledon-flowering medium at a concentration of about 0.5 mg/L to about 5.0 mg/L (and any concentration within that range), alone or in combination with a cytokinin. A preferred concentration of a substituted phenylurea cytokinin analog is about 0.75 mg/L to about 4.0 mg/L. A more preferred concentration is about 0.75 mg/L to about 3.0 mg/L. An especially preferred concentration of a substituted phenylurea cytokinin analog is about 0.75 mg/L to about 2.5 mg/L. A most preferred concentration of a substituted phenylurea cytokinin analog is about 1.0 mg/L to about 2.0 mg/L.

In preferred embodiments, a substituted phenylurea cytokinin analog is TDZ and is present in a cotyledon-shoot-flowering medium at a concentration of about 0.1 mg/L to about 5.0 mg/L (and any concentration within that range), alone or in combination with a cytokinin. A preferred concentration of TDZ is about 0.75 mg/L to about 4.0 mg/L. A more preferred concentration is about 0.75 mg/L to about 3.0 mg/L. An especially preferred concentration of TDZ is about 0.75 mg/L to about 2.5 mg/L. Another preferred concentration 1.0 mg/L to about 2.0 mg/L. A most preferred concentration of TDZ is about 1.0 mg/L.

A cotyledon-shoot-flowering medium may also comprise a cytokinin as described above, or mixtures thereof. A cytokinin may be present in a cotyledon-shoot-flowering medium at a concentration from about 0.5 mg/L to about 4.0 mg/L (and any concentration within that range). A preferred concentration is about 1.0 mg/L to about 4.0 mg/L. A more preferred concentration is about 2.0 mg/L to about 3.75 mg/L. An especially preferred concentration of a cytokinin is about 2.5 mg/L to about 3.5 mg/L. A most preferred concentration of a cytokinin is about 3.0 mg/L.

In preferred embodiments, a cytokinin is BAP and may be present in a cotyledon-shoot-flowering medium at a concentration from about 0.5 mg/L to about 4.0 mg/L (and any concentration within that range). A preferred concentration of BAP is about 1.0 mg/L to about 4.0 mg/L. A more preferred concentration is about 2.0 mg/L to about 3.75 mg/L. An especially preferred concentration of BAP is about 2.5 mg/L to about 3.5 mg/L. A most preferred concentration of BAP is about 3.0 mg/L.

BAP at a concentration of 3.0 mg/L (without TDZ) produces high frequency of shoots with low frequency of fertile flowers and viable seeds whereas the combination treatment with TDZ at a concentration of 1.0 mg/L to 2.0 mg/L with 3.0 mg/L BAP produces shoots with high frequency of fertile flowers and viable seeds. Accordingly, a preferred cotyledon-shoot-flowering medium comprises BAP at a concentration of about 3.0 mg/L and TDZ at a concentration from about 1.0 to 2.0 mg/L. An especially preferred cotyledon-shoot-flowering medium comprises BAP at a concentration of about 3.0 mg/L and TDZ at a concentration of 1.0 mg/L.

A cotyledon-shoot-flowering medium is prepared as described above regarding a cotyledon-flowering medium.

Direct Flower Bud and Viable-Seed Production from Radicle Explants

In a radicle-flowering method, seeds are washed and sterilized and transferred to culture plates containing $MSB_5$ medium. The seeds are allowed to germinate, preferably for about three days. After germination, the seed coat is removed and the cotyledons are detached from the seedling. Portions of the radicle and plumule at the proximal end of the cotyledons are excised. At this point in time, a radicle may be transformed with a gene of interest by any suitable method known in the art or as described herein. A radicle or portions thereof are placed on a radicle-flowering medium, which is another embodiment of the invention and is described below. A radicle-flowering medium preferably comprises a substituted phenylurea cytokinin analog, or mixtures thereof, and a cytokinin, or mixtures thereof.

A radicle is preferably incubated on a radicle-flowering medium at 25±2° C. under a light/dark (16/8 hour) photoperiod provided by cool-white fluorescent lights at a quantum flux density of 30 µmol $s^{-1}m^{-2}$.

After sufficient time (usually about 15 days) to allow flower bud formation, radicle explants are removed from a radicle-flowering medium and placed on hormone free $MSB_5$ medium and placed in light. From the cut end, direct flower buds are observed when a radicle explant is incubated on a radicle-flowering medium. See example 3 and FIGS. 3a-3d for direct viable-seed producing flower bud production directly from radicle explants.

Radicle-Flowering Medium

Another embodiment of the invention provides a radicle-flowering medium comprising $MSB_5$ medium supplemented with either a substituted phenylurea cytokinin analog (as described above), or mixtures thereof and/or in combination with a cytokinin (as described above) or mixtures thereof. A radicle placed on a radicle-flowering medium produces flower buds that produce fertile seed. A substituted phenylurea cytokinin analog may be present in a radicle-flowering medium at a concentration of about 0.1 mg/L to about 5.0 mg/L (and any concentration within that range), alone or in combination with a cytokinin and/or auxin as described below. A preferred concentration of a substituted phenylurea cytokinin analog is about 1.0 mg/L to about 4.0 mg/L. A more preferred concentration is about 1.5 mg/L to about 3.0 mg/L. An especially preferred concentration of a substituted phenylurea cytokinin analog is about 1.5 mg/L to about 2.5 mg/L. A most preferred concentration of a substituted phenylurea cytokinin analog is about 2.0 mg/L.

In preferred embodiments, a substituted phenylurea cytokinin analog is TDZ and is present in a radicle-flowering medium at a concentration of about 0.1 mg/L to about 5.0 mg/L (and any concentration within that range), alone or in combination with a cytokinin and/or auxin as described below. A preferred concentration of TDZ is about 1.0 mg/L to about 4.0 mg/L. A more preferred concentration of TDZ is about 1.5 mg/L to about 3.0 mg/L. An especially preferred concentration of TDZ is about 1.5 mg/L to about 2.5 mg/L. A most preferred concentration of TDZ is about 2.0 mg/L.

A radicle-flowering medium may also cytokinins as described above. A cytokinin may be present in a radicle-flowering medium at a concentration from about 0.5 mg/L to about 4.0 mg/L (and any concentration within that range). A preferred concentration is about 0.5 mg/L to about 3.0 mg/L. A more preferred concentration is about 0.75 mg/L to about 2.5 mg/L. An especially preferred concentration of cytokinin is about 0.75 mg/L to about 1.5 mg/L.

In preferred embodiments a cytokinin is BAP and may be present in a radicle-flowering medium at a concentration of about 0.5 mg/L to about 4.0 mg/L (and any concentration within that range). A preferred concentration of BAP is about 0.5 mg/L to about 3.0 mg/L. A more preferred concentration of BAP is about 0.75 mg/L to about 2.5 mg/L. An especially preferred concentration of BAP is about 0.75 mg/L to about 1.5 mg/L. A most preferred concentration of BAP is about 1 mg/l In a preferred embodiment, a radicle-flowering medium comprises TDZ at about 2.0 mg/L and BAP about 1.0 mg/L.

A radicle-flowering medium may also comprise auxins as described above regarding a cotyledon-flowering medium.

A radicle-flowering medium is prepared as described above regarding a cotyledon-flowering medium.

Fertile Flower Bud and Viable-Seed Production from in vitro Developed Shoots from Radicle Explants Another embodiment of the present invention provides a method for eliciting fertile flower and viable seed production from in vitro developed shoots originating from the radicle explants.

In a radicle-shoot-flowering method, seeds are washed and sterilized and transferred to culture plates containing $MSB_5$ medium. The seeds are allowed to germinate and preferably for about three days. After germination, the seed coat is removed and the cotyledons are detached from the seedling. Portions of the radicle and plumule at the proximal end of the cotyledons are excised. At this point in time, a radicle may be transformed with a gene of interest by any suitable method known in the art or as described herein. A radicle or portions thereof are placed on a radicle-shoot-flowering medium, which is another embodiment of the invention and is described below.

A radicle is preferably incubated on a radicle-shoot-flowering medium at 25±2° C. under a light/dark (16/8 hour) photoperiod provided by cool-white fluorescent lights at a quantum flux density of 30 µmol $s^{-1}m^{-2}$. After sufficient time (usually about 15 days) to allow flower bud formation, a radicle explant is removed from a radicle-shoot-flowering medium and placed on $MSB_5$ and placed in light. From the cut end, direct multiple shoots are observed when a radicle explant is incubated on a radicle-shoot-flowering medium. From these shoots, flower buds and viable seeds are produced. See example 4 and FIGS. 4a-4d for direct viable-seed producing flower bud production from shoots developed on radicle explants.

Radicle-Shoot-Flowering Medium

Another embodiment of the invention provides a radicle-shoot-flowering medium comprising $MSB_5$ medium supplemented with a substituted phenylurea cytokinin analog (as described above) or mixtures thereof. A radicle placed on a radicle-shoot-flowering medium produces shoots, which produce flower buds that produce fertile seed. A radicle-shoot-flowering medium of the present invention may further comprise a cytokinin as described above, or mixtures thereof. A substituted phenylurea cytokinin analog may be present in a radicle-shoot-flowering medium at a concentration of about 0.5 mg/L to about 5.0 mg/L (and any concentration within that range), alone or in combination with a cytokinin and/or auxins as described below. A preferred concentration of a substituted phenylurea cytokinin analog is about 0.75 mg/L to about 4.0 mg/L. A more preferred concentration is about 0.75 mg/L to about 3.0 mg/L. An especially preferred concentration of a substituted phenylurea cytokinin analog is about 0.75 mg/L to about 2.5 mg/L. A most preferred concentration of a substituted phenylurea cytokinin analog is about 1.0 mg/L to about 2.0 mg/L.

In preferred embodiments, a substituted phenylurea cytokinin analog is TDZ and is present in a radicle-shoot-flowering medium at a concentration of about 0.1 mg/L to about 5.0 mg/L (and any concentration within that range), alone or in combination with a cytokinin and/or auxin as described below. A preferred concentration of TDZ is about 0.75 mg/L to about 4.0 mg/L. A more preferred concentration is about 0.75 mg/L to about 3.0 mg/L. An especially preferred concentration of TDZ is about 0.75 mg/L to about 2.5 mg/L. A most preferred concentration of TDZ is about 1.0 mg/L to about 2.0 mg/L.

A radicle-shoot-flowering medium may also comprise cytokinins as described above. A cytokinin may be present in a radicle-shoot-flowering medium at a concentration from about 0.5 mg/L to about 4.0 mg/L (and any concentration within that range). A preferred concentration is about 1.0 mg/L to about 4.0 mg/L. A more preferred concentration is about 2.0 mg/L to about 3.75 mg/L. An especially preferred concentration of cytokinin is about 2.5 mg/L to about 3.5 mg/L.

In preferred embodiments, a cytokinin is BAP and may be present in a radicle-shoot-flowering medium at a concentration from about 0.5 mg/L to about 4.0 mg/L (and any concentration within that range). A preferred concentration of BAP is about 1.0 mg/L to about 4.0 mg/L. A more preferred concentration is about 2.0 mg/L to about 3.75 mg/L. An especially preferred concentration of BAP is about 2.5 mg/L to about 3.5 mg/L. A most preferred concentration of BAP is about 3 mg/L.

In a preferred embodiment, a radicle-shoot-flowering medium comprises TDZ at about 1.0 mg/L to about 2.0 mg/L and BAP at about 3.0 mg/L.

A radicle-shoot-flowering medium is prepared as described above regarding a cotyledon-flowering medium.

Fertile Flower Buds and Viable Seed Production from in vitro Developed Shoots from from Leaf Explants Another embodiment of the invention provides a method for producing viable seeds from in vitro developed shoots and flower buds from leaf explants. Any leaf explant of interest may be used (including leaves from monocots or dicots). In addition to using a leaf explant that may or may not be transformed with any suitable method known in the art, a leaf explant from a transgenic plant (thus already having a gene of interest) may also be used. Leaf explants are prepared and sterilized by techniques known in the art. After sterilization, preferably with 0.1% sodium hypchlorite solution, leaf explants are placed on an in vitro shoot multiplication medium (which is another embodiment of the invention and described below) comprising a cytokinin and auxin. Shoots begin to form within two weeks. After the shoots are allowed to multiply, they are placed on an in vitro shoot elongation medium (which is another embodiment of the invention and described below) comprising a gibberellic acid to allow shoot elongation. After shoot elongation, shoots may be placed on MS medium with or without indole-3-butyric acid ("IBA") to allow rooting. Flower buds develop on the elongated shoots and develop viable seed.

This invention was made, at least in part, with government support under USDA-ARS Grant No. 5836071193. The U.S. government has certain rights in the invention.

In vitro Shoot Multiplication Medium

Another embodiment of the invention provides an in vitro shoot multiplication medium comprising MS medium supplemented with an auxin and a cytokinin as described above, or mixtures thereof. Leaf explants placed on an in vitro shoot multiplication medium develop shoots in roughly two weeks.

An auxin, or mixtures thereof, may be present in an in vitro shoot multiplication medium at a concentration from about 0.0125 mg/L to about 1.0 mg/L (and any concentration within that range). A preferred concentration of an auxin is about 0.025 mg/L to about 0.5 mg/L. A more preferred concentration of an auxin is about 0.05 mg/L to about 0.25 mg/L. A most preferred concentration of auxin is about 0.1 mg/L.

In preferred embodiments, an auxin is IAA and may be present in an in vitro shoot multiplication medium at a concentration from about 0.0125 mg/L to about 1.0 mg/L (and any concentration within that range). A preferred concentration of IAA is about 0.025 mg/L to about 0.5 mg/L. A more preferred concentration of IAA is about 0.05 mg/L to about 0.25 mg/L. A most preferred concentration of IAA is about 0.1 mg/L.

A cytokinin may be present in an in vitro shoot multiplication medium at a concentration from about 0.5 mg/L to about 3.0 mg/L (and any concentration within that range). A preferred concentration is about 1.0 mg/L to about 2.5 mg/L. A more preferred concentration is about 1.5 mg/L to about 2.25 mg/L. An especially preferred concentration of cytokinin is about 1.75 mg/L to about 2.25 mg/L. A most preferred concentration of cytokinin is about 2.0 mg/L.

In preferred embodiments, a cytokinin is BAP and may be present in an in vitro shoot multiplication medium at a concentration from about 0.5 mg/L to about 3.0 mg/L (and any concentration within that range). A preferred concentration of BAP is about 1.0 mg/L to about 2.5 mg/L. A more preferred concentration of BAP is about 1.5 mg/L to about 2.25 mg/L. An especially preferred concentration of BAP is about 1.75 mg/L to about 2.25 mg/L. A most preferred concentration of BAP is about 2.0 mg/L.

An in vitro shoot multiplication medium is prepared as described above regarding a cotyledon-flowering medium.

In vitro Shoot Elongation Medium

Another embodiment of the invention provides an in vitro shoot elongation medium comprising MS medium supplemented with a gibberellin such as, but not limited to GA1, GA3, GA4, GA5, GA9 and GA20. In vitro generated shoots placed on an in vitro shoot elongation medium will elongate. A gibberellin may be present at a concentration of about 0.01 mg/L to about 5.0 mg/L. A preferred gibberellin is GA3 at a preferred concentration of about 0.5 mg/L.

Combination of in vitro Flowering with Transformation

The present invention also provides an efficient, environmentally friendly and low-cost production of transgenic plants and seeds, which may express one or more value added traits and/or products, including desirable agronomic traits, pharmaceuticals or other HIP. In this embodiment, in vitro flowering methods described above are combined with transformation methods known in the art to quickly produce transgenic plants. Using methods of the present invention, transgenic seed development can occur entirely within a closed culture environment, and contamination by transgenic pollen from T, plants is entirely eliminated. Notably, as worldwide annual pharmaceutical product needs can be met using greenhouse acreage, future contamination by transgenic pollen of standard crop plants or their wild relative is likewise minimized. The methods of the present invention relating to in vitro flowering is genotype independent and is applicable across taxa. The production of transgenics through in vitro flowering is particularly efficacious in producing HIP at a vastly decreased cost in a environmentally friendly way that is not only rapid but also eliminates entirely the possibility of any contamination from transgenic pollen during the production of foundation seed.

In particular, using the methods of in vitro flowering of the present invention to produce transgenic plants, a sterilized seed that contains intact cotyledons is germinated on an appropriate MS-type basal media for at time sufficient for the seed to bulge the cotyledons. Preferably, the seed is germinated for three to five days. Cotyledons may be transformed with at least one gene of interest encoding the value-added traits and/or products, using any suitable method known in the art including, but not limited to, nuclear transformation, agrobacterium transformation, chloroplast transformation, whisker mediated transformation, electroporation, and biolistics.

One preferred method of transformation involves agrobacterium-mediated transformation as described in U.S. patents: Chee et al. U.S. Pat. No. 5,376,543; Chee et al. U.S. Pat. No. 5,169,770; Goldman et al. U.S. Pat. Nos. 6,020,539; 5,187,073 and 5,177,010. These patents are herein incorporated by reference in their entirety.

A nucleic acid of choice may encode any desired biomolecule, but of particular interests are HIP, and/or may encode desired genes of interest that cause the expression of desirable agronomic traits, such as, but not limited to, stress, drought, cold and salt tolerance. The nucleic acids also preferably contain regulatory sequences operably linked to allow production/expression of the gene(s) of interest. Such regulatory sequences are well known in the art and include enhancers and promoters such as inducible, constitutive, and tissue-specific promoters.

Alternatively, cotyledons may be used as a choice explant for direct gene transfer into the chloroplasts, nuclei and/or mitochondria. Cotyledons are considered a preferred explant for transfer of foreign DNA into legumes, and in particular soybeans. Two methods of transfer of DNA into organelles of plants are commonly practiced. One method involves inserting DNA into the nucleus and the other involves inserting DNA into the chloroplast. In the case of nuclear transformation, there exists a possibility for segregation, multiple gene copies and instability in further generations of transgenic plants. In contrast, chloroplast transformation, involves maternal inheritance as the DNA is directed to chloroplasts.

With the chloroplast transformation, a vector encoding the gene(s) of interest is inserted into the plastid genome. Suitable vectors, as well as particle bombardment criteria, are known in the art to achieve maximum insertion of the gene(s) of interest into the plastid. It is appreciated by those skilled in the art that plastids possess the proper machinery to fold eukaryotic proteins and add disulfide bonds to generate a usable gene(s) of interest.

Chloroplast transformation technologies are a promising tool in biotechnology and have the potential to solve some of the problems associated with traditional plant genetic engineering. One major environmental concern is the escape of foreign genes through pollen transmission to wild relatives. With the advent of herbicide resistant crops, such as canola, there is public concern about the production of superweeds that are resistant to herbicides. The genetic engineering of chloroplasts provides for containment of this gene pollution.

In addition, chloroplast is an ideal organelle for expression of value added traits and/or products. A typical plant cell contains approximately 100 chloroplasts and each chloroplast contains about 100 copies of the identical plastid genome. Therefore, a single gene is represented at least 10,000 times within a plant cell and its capacity as a bioreactor appears unmatched. Moreover, even though transgenic chloroplasts may be present in pollen, the foreign gene will not escape to other crops because chloroplast DNA is not passed onto the egg cell.

Chloroplast transformation methods are known in the art and are presented in various U.S. patent including U.S. Pat. Nos. 5,693,507; 5,932,479; 6,642,053; 5,451,513 and 6,388,168. Methods of chloroplast transformation include biolistics and polyethylene glycol (PEG)-mediated transformation. Additionally, chloroplast specific vectors have been developed to facilitate the incorporation of transgenes into the chloroplast genome.

Thus, in one embodiment of the invention, the in vitro flowering methods of the present invention are combined with chloroplast transformation. Using this method, the time for transgenic plant generation may be substantially reduced as compared to the time normally required for transgenic plant formation. In this method, before the cotyledons are placed on the in vitro flowering medium of the present invention they are subjected to chloroplast transformation. After chloroplast transformation, it is preferable to utilize an in vitro flowering medium of the present invention that induces shoot development. In addition to the reduction in production time to form transgenic plants expressing the gene(s) of interest, the chloroplast transformation in combination with an in vitro flowering method, provides multiple advantages including site-specific integration, lack of transgene silencing, transgene containment because of maternal inheritance, and high levels of transgenic expression.

After transformation, cotyledons are transferred to an in vitro flowering media of the present invention. The cotyledon is allowed to develop at least one flower bud, or multiple shoots, as discussed previously, all of which lead to viable-seed producing flowers. The transgenic bud or shoots (as well as the seeds and plants generated from these seeds) express the gene(s) of interest and can be harvested to obtain the value added traits and/or products.

Another preferred method of transformation relates to a rapid, dependable, and high frequency regeneration method, which is universal to both monocotyledonous and dicotyledonous species, and is independent of whether or not the meristem of the monocots and/or dicots are transgenic. This method is disclosed in Goldman and Sairam, U.S. patent application Ser. No. 10/480,865 filed on Dec. 12, 2003, and WO 02/102979 entitled "Methods for Transformation of Mono- and Dicotyledonous Plants Using Meristematic Tissue," which references are herein incorporated by reference in their entireties.

The method disclosed in U.S. patent application Ser. No. 10/480,865 involves producing mono- or dicotyledonous plant cell or tissues with one or more genes of interest. An undifferentiated shoot and/or meristem cell or tissue of the plant is incubated in a medium containing at least one growth regulator that promotes cell elongation, such as auxin, 2,4-D, dicamba, IAA, picloram, NAA, IPA, IBA, PAA, BFA or PBA. The shoot and/or root meristem cell or tissue is infected with a non-supervirulent agrobacterium containing at least one gene of interest covalently linked to T-DNA. The infected shoot and/or root meristem cell or tissue is regenerated in a culturing medium and grown to produce a transformed plant.

Optionally, the infected shoot and/or root meristems are regenerated into a plant by organogenesis. The infected shoot and/or root meristems may be then cultured in light on a medium that contains at least one plant growth hormone that promotes cell division to induce shoot and/or root formation to form transformed plants. Alternatively, the infected shoot and/or root meristems are regenerated into a plant by somatic embryogenesis. This method may further comprise culturing the infected shoot and/or root meristems in the dark to induce callus formation and somatic embryo formation.

The method disclosed in WO 02/102979 and U.S. patent application Ser. No. 10/480,865 (entitled "Method for transformation of Mono-and Di-Cotyledonous plants using Meristematic Tissue and Nodal Callus from Di-Cotyledonous Plants") involves germinating the seed for four or five days on a tissue culture medium containing a growth regulator that induces cell elongation, such as, but not limited to, auxin. The germinating seed produces either shoots and/or root tissue each of which comprises a complete meristem. The cotyledonary node, shoot or root tissue is then infected with agrobacterium containing at least one gene of interest. The agrobacterium is incubated in the presence of at least one phenolic compound such as acetosyringone. The phenolic compound is used to induce the Vir complex that in turn results in T-DNA transfer of the gene of interest. This method of transformation provides a high frequency of transformation.

In addition to transforming cotyledons, radicles, shoots and leaf explants may also be transformed with a gene of interest using any suitable method known in the art. The transformed radicles, shoots and leaf explants may then be used in the various in vitro flowering methods of the present invention.

Use of in vitro Flowering for DNA Markers-Assisted Breeding

In vitro flowering can be used for DNA marker-assisted breeding to reduce the life cycle of seed production. DNA marker-assisted breeding may be used to generate novel germplasms that express multiple value-added traits. One such example is to produce a soybean line that is resistant to all known races of cyst nematode and that increases the accumulation of protein in the cotyledon. Such lines may be produced rapidly through the use of in vitro flowering technology.

The cyst nematode resistant line PUSCN14 is crossed to the high protein line C1973. The resulting $F_1$ is planted to produce $F_2$ seed, which in turn is screened in the greenhouse for SCN resistance. Those plants that survive are selfed to generate a replicate segregating $F_3$, which are tested for seed protein concentration using Near Infrared Transmittance ("NIR"). The advantage of NIR is that it is not destructive to the seed.

The Shoemaker lab has developed a detailed soybean genetic map that includes a wide variety of molecular markers. Among those loci placed are RFLPs, SSRs, RAPDs and AFLPs (Keim et al., 1990; Shoemaker et al., 1992; Shoemaker et al., 1996, soybean data base). Many hundreds of these markers are in the public domain and are of sufficient number to screen the entire soybean genome for polymorphism. In this connection, Vierling et al. (1995) successfully identified four RFLPs, A006, A567, A487, and A112 that were associated with SCN resistance. Of the 211 RFLPs screened, 53 were polymorphic and sufficient to identify one new major resistance locus and two minor ones.

Identifying loci controlling soybean protein concentration is feasible since the RFLPs associated with SCN resistance are already known, and since the $F_2$ plants are already screened for disease resistance. The principle is to identify particular genetic polymorphisms that segregate with high seed protein concentration. In this connection, $F_3$ seed need only be scored for increases in percent protein. Such a strategy will identify a unique culture that will express disease resistance and will increase protein/seed unit and yield.

EXAMPLES

Example 1

Direct Fertile Flower Bud and Viable-Seed Production on Cotyledon

Healthy soybean seeds are hand picked and washed with a few drops of soap (Linquinox, Fischer scientific, Pittsburgh, Pa.) for 10 minutes in running tap water. The seeds are then sterilized in 70% ethyl alcohol for 1 min and treated with 0.1% (w/v) mercuric chloride for 10 min. Sterilized seeds are again washed for three times at five minute intervals with sterilized distilled water, and plated six seed on each petri plate containing 20 ml of $MSB_5$ medium. Three-day-old aseptic seedlings are used as the source material for explant preparation. Six isolated cotyledons are plated on each culture plate in such a way that the abaxial side in contact with the medium. $MSB_5$ medium supplemented with different concentrations of TDZ (0.1, 0.5, 1.0, 2.0 and 5.0 mg/L) either alone, or in combination, with BAP (1.0-4.0 mg/L) are tested for flower induction. The media is augmented with 3% (w/v) sucrose and solidified with 0.56% agar (Phytotech Labs). The pH of the medium is adjusted to 5.8 with 0.1M NaOH or 0.1M HCl before autoclaving at 1.4 kg $cm^{-2}$ for 20 min at 121° C. The cultures are incubated in light-dark (16-8 hrs) photoperiodic conditions of cool-white-fluorescent light providing a quantum flux density of 30 mol $s^{-1}m^{-2}$ at 25±2° C. Explants with or without multiple flower buds are subcultured regularly at 20 days interval to fresh medium. Within 15 days of culture initiation, the bulging of cotyledons and induction of deep greenish unorganized structures from the proximal end is noticed.

FIGS. 1a-1d are photographs showing direct viable-seed producing flower bud production in soybean. More specifically, FIG. 1a is a photograph of is the proximal end of cotyledon showing flowers and flower buds. FIG. 1b is a photograph of an individually dissected flower buds (70-80) from a single cotyledon. FIG. 1c is a photograph of the proximal end of the cotyledon showing pods. FIG. 1d is a photograph of a mature pod and viable seed.

Example 2

Fertile Flower Bud and Viable Seed Production from in vitro Developed Shoots from Cotyledons Healthy soybean seeds are hand picked and washed with a few drops of soap (Linquinox, Fischer scientific, Pittsburgh, Pa.) for 10 minutes in running tap water. The seeds are then sterilized with 70% ethyl alcohol for 1 min followed by a ten minute treatment with 0.1% (w/v) mercuric chloride. Sterilized seeds are again washed for three times at five minute intervals with sterilized distilled water, and plated 6 seed on each petri plate containing 20 ml of $MSB_5$ medium. Three-day-old aseptic seedlings are used as the source material for explant preparation. Six isolated cotyledons are plated on each culture plate in such a way that the abaxial side in contact with the medium. $MSB_5$ medium supplemented with different concentrations of TDZ (0.1, 0.5, 1.0, 2.0 and 5.0 mg/L) either alone, or in combination with, BAP (1.0-4.0 mg/L) are tested for flower induction. The media is augmented with 3% (w/v) sucrose and solidified with 0.56% agar (Phytotech Labs). The pH of the medium is adjusted to 5.8 with 0.1M NaOH or 0.1M HCl before autoclaving at 1.4 kg $cm^{-2}$ for 20 min at 121° C. The cultures are incubated in light-dark (16-8 hrs) photoperiodic conditions of cool-white-fluorescent light providing a quantum flux density of 30 mol $s^{-1}m^{-2}$ at 25±2° C. Explants with or without multiple shoots are subcultured regularly at 20 days interval to fresh $MSB_5$ medium. After six weeks in culture, flower buds are noticed on in vitro developed shoots.

FIGS. 2a-2b are photographs showing direct viable-seed producing flower bud production from in vitro developed shoots from cotyledons in soybean. Specifically, FIG. 2a is a photograph of an in vitro regenerated shoot showing flowers. FIG. 2b is a photograph of an in vitro regenerated shoot showing flowers and pods.

Example 3

Direct Fertile Flower Bud and Viable-Seed Production from Radicle Explants

Healthy soybean seeds are handpicked and washed in running tap water with few drops of soap (Linquinox, Fischer scientific, Pittsburgh, Pa.) for 10 minutes. The seeds are then surface sterilized with 70% alcohol for one min followed by 0.1% (w/v) mercuric chloride for 10 min. After the treatment, seeds are washed thoroughly for 3 times at 5-minute intervals with sterilized distilled water. Sterilized seeds (6 per plate) are transferred to culture plates (100×150 mm) containing 20 ml of modified $MSB_5$ vitamins solidified with 0.56% agar (Phytotech Labs) for germination. The pH of the media is adjusted to 5.8 with 0.1 M NaOH or 0.1 M HCl before autoclaving at 1.4 kg $cm^{-2}$ for 20 min at 121° C. The seeds are incubated in dark at 25±2° C. for 3 days.

After 3 days of seed germination, the seed coat is carefully removed with a sterile forceps, and cotyledons are detached from the seedling using surgical blades. Portions of radicle and plumule at the proximal end of the cotyledons are excised. Radicle explants are then placed on each culture plate containing modified MS medium supplemented either with different concentrations of TDZ alone, or in combination with BAP. The concentrations are as described in earlier examples involving the cotyledons. The cultures are incubated at 25±2° C. under light-dark (16/8 hour) photoperiod provided by cool-white fluorescent lights at a quantum flux density of 30-µmol $s^{-1}m^{-2}$. After 15 days of incubation (green flower buds are formed), radicle explants are removed from hormone medium and placed on hormone free $MSB_5$ medium and placed in light.

From cut end, distal to the root, direct flower buds are observed. FIGS. 3a-3d are photographs showing direct viable-seed producing flower bud production from radicle explants in soybean. Specifically, FIGS. 3a and 3b are photographs of the cut end of radicles showing direct flowers and flower buds. FIGS. 3c and 3d are close up photographs of flowers and flower buds on the radicle explant

Example 4

Fertile Flower Bud and Viable-Seed Production from in vitro Developed Shoots from Radicle Explants Healthy soybean seeds are hand picked and washed in running tap water with a few drops of soap (Linquinox, Fischer scientific, Pittsburgh, Pa.) for 10 minutes. The seeds are then surface sterilized with 70% alcohol for one min followed by 0.1% (w/v) mercuric chloride for 10 min. After the treatment, seeds are washed thoroughly for three times at 5-minute intervals with sterilized distilled water. Sterilized seeds (6 per plate) # are transferred to culture plates (100×150 mm) containing 20 ml of modified $MSB_5$ solidified with 0.56% agar (Phytotech Labs) for germination. The pH of the media is adjusted to 5.8 with 0.1 M NaOH or 0.1 M HCl before autoclaving at 1.4 kg cm$^{-2}$ for 20 min at 121° C. The seeds are incubated in dark at 25+2 ° C. for 3 days.

After three days of seed germination, the seed coat is carefully removed with a sterile forceps, and cotyledons are detached from the seedling using surgical blades. Portions of radicle and plumule at the proximal end of the cotyledons are excised. Radicle explants are then placed on each culture plate containing modified MS medium supplemented with different concentrations of TDZ, alone or in combination, with BAP. The concentrations are as described in earlier examples involving cotyledons. The cultures are incubated at 25±2° C. under light-dark (16/8 hour) photoperiod provided by cool-white fluorescent lights at a quantum flux density of 30-μmol s$^{-1}$m$^{-2}$. After 15 days of incubation, the radicle explants are removed from hormone medium and placed on $MSB_5$ medium and placed in light.

From cut end, distal to the root, direct shoots are observed. FIGS. 4a-4d are figures showing viable-seed producing flower bud production from in vitro developed shoots from radicle explants in soybean. Specifically, FIGS. 4a and 4b are photographs of the cut end of the radicle showing in vitro regenerated plant. FIGS. 4c and 4d are photographs of an in vitro regenerated plant from radicle showing flowers and pods.

Example 5

In vitro Flowering in Other Dicots such as Chrysanthemum

In *Chrysanthemum palludosum*, flowers are induced directly from in vitro developed shoots derived from leaf or stem explants after transferring them from a media containing BAP and IAA to a media devoid of any growth regulators. This system has been shown to be rapid (8-10 weeks) and repeatable.

Leaves and stem explants from 4-8 week-old plants are surface sterilized by washing with soap and running tap water, followed by rinsing with commercial bleach (Clorox) solution (0.1% sodium hypochlorite final concentration) for 5-8minutes with continuous agitation in the flow hood. Explants are then rinsed 4-5 times with autoclaved MilliQ water; blot dried on autoclaved filter papers and cultured in 100×15 mm Petri plates. Explants are cultured on $MSB_5$ medium with 3% sucrose and 0.7% agar supplemented with different concentrations of BAP (0.5-2.0 mg/L), IAA (0.1-2.0 mg/L), or TDZ (0.5-2.0 mg/L) alone, or with different combinations of BAP (0.5-2.0 mg/L) and IAA (0.1 mg/L), or BAP (0.1-3.0 mg/L) and TDZ (0.1-1.0 mg/L).

FIGS. 5a-f are photographs showing in vitro regeneration and flowering of *chrysanthemum palludosum*. FIG. 5a is a photograph showing shoot bud differentiation from a stem explant. FIG. 5b is a photograph showing shoot bud differentiation from a leaf explant. FIGS. 5c and 5d show shoot bud multiplication and elongation. FIGS. 5e-5f show in-vitro flowering and rooting.

Example 6

In vitro Flowering in Another Dicot—*Centaurea montana*

Flower buds are induced in *Centaurea cyanus* in vitro after shifting the elongated shoots from a media containing BAP and IAA to a hormone free MS basal medium. The flower buds are able to open and bloom inside the test tube, thus enabling one to shorten the life cycle of the plant and obtain sterile seeds in vitro. Cm$^2$ leaf explants are the starting material for in vitro regeneration systems.

Leaf segments are cut from plants grown in the greenhouse and are surface sterilized by rinsing with 0.1% sodium hypochlorite solution followed by several washes with autoclaved MilliQ water. Explants are tested for shoot multiplication on MS media containing different combinations of BAP and IAA. A preferred medium for shoot multiplication contains 0.1 mg/L IAA and 2.0 mg/L BAP. Using this medium, shoots start to form within two weeks of culture initiation. After two to four weeks, the shoots start to multiply. The shoots are at 25±2° C. under light-dark (16/8 hour) photoperiod provided by cool-white fluorescent lights at a quantum flux density of 30-μmol s$^{-1}$m$^{-2}$. Shoot elongation is carried on MS media containing different concentrations of $GA_3$ (Gibberellin) and rooted on MS basal media with or without IBA.

FIGS. 6a-f show in vitro regeneration and flowering of *Centaurea monatana* and *Centaurea cyanus*. FIG. 6a shows shoot bud differentiation from a leaf explant. FIGS. 6b and 6c show shoot bud multiplication and elongation. FIGS. 6d,6e and 6f show plantlet elongation, in-vitro flowering and rooting, respectively.

Example 7

In vitro Flowering from Leaf Explant of Petunia

Figure 7:
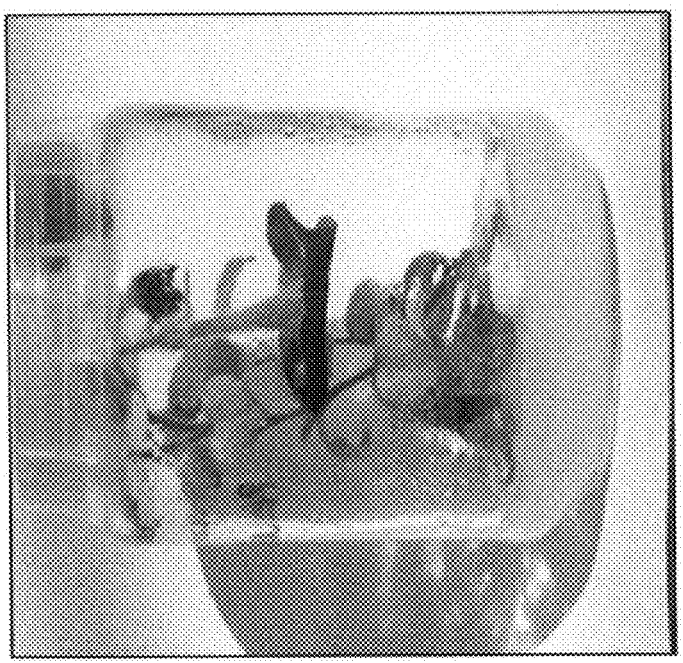
FIG. 7 is a photograph of in vitro regeneration and flowering of petunia.

Leaf segments from a petunia were sterilized using the sterilization procedures described above and placed on MS basal medium supplemented with different concentrations of TDZ (0.1, 0.5, 1.0, 2.0 and 5.0 mg/L) either alone or in combination with BAP (3.0 mg/L) or on a MS basal medium with no hormones. Multiple flower buds were induced in 4 weeks on all the media tested. A large number of flowers were induced on MS basal medium. FIG. 7 is a photograph showing in vitro flowering in a petunia.

All references cited herein, including journal articles, patents, patent applications, and databases are expressly incorporated by reference into this application in order to more fully describe the state of the art to which this invention pertains.

The above detailed description of the present invention is given for explanatory purposes. It will be apparent to those skilled in the art that numerous changes and modifications can be made without departing from the scope of the invention. Accordingly, the whole of the foregoing description is to be construed in an illustrative and not a limiting sense, the scope of the invention being defined solely by the appended claims.

The invention claimed is:

1. A method for eliciting direct flower bud production in vitro on a soybean cotyledon, the method comprising 1) germinating at least one seed on a medium comprising MS and B$_5$ vitamins in amounts effective to cause formation of the soybean cotyledon,
2) splitting the soybean cotyledon,
3) transferring the split cotyledon to a cotyledon-flowering medium comprising:
   i) benzlamino purine (BAP) present at a concentration of about 0.75 mg/L to about 1.5 mg/L, and
   ii) 1-phenyl-3-(1,2,3-thidiazol-5-yl)urea (TDZ) present at a concentration of about 1.5 mg/L to about 2.5 mg/L,
   wherein the BAP and the TDZ are present in concentrations whereby no intervening shoot is formed on the cotyledon;
4) allowing the split cotyledon to develop at least one flower bud directly on the cotyledon, and
5) selecting for an in vitro flower formed directly on the split cotyledon.

2. The method of claim 1 wherein TDZ is present at a concentration of about 2.0 mg/L.

3. A method of claim 1 wherein BAP is present at a concentration of about 1 mg/L.

4. The method of claim 1 wherein the concentration of TDZ in the cotyledon-flowering medium is about 2.0 mg/L and the concentration of BAP in the cotyledon-flowering medium is about 1.0 mg/L.

5. The method of claim 1, further comprising allowing the flower bud to develop seed.

* * * * *